United States Patent

Plant Pat. 3,982

Patented Nov. 16, 1976

1

3,982

STRAWBERRY PLANT

Harold A. Johnson, Jr., Watsonville, Calif., assignor to Driscoll Strawberry Associates, Inc., Watsonville, Calif.

Filed Dec. 4, 1975, Ser. No. 637,802

Int. Cl.[2] A01H 5/03

U.S. Cl. Plt.—49 1 Claim

Figure 1:
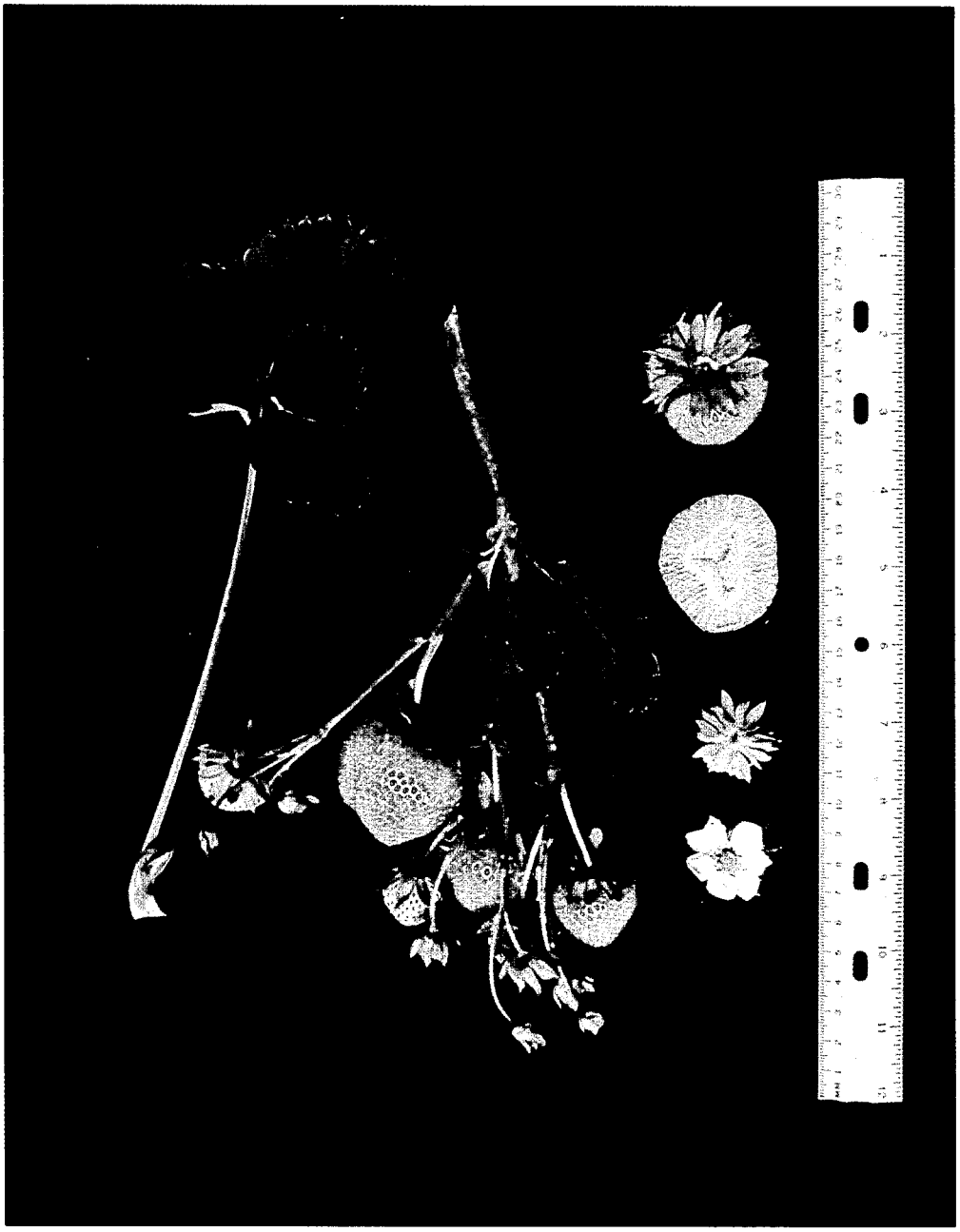

This invention relates to a new and distinct variety of strawberry plant known as E21 and which is the result of a cross of the everbearing Driscoll Associates Variety E3, Plant Pat. 2,891 and the Driscoll Strawberry Associates F5, Plant Pat. 2,892.

The seedlings resulting from the aforementioned cross were grown and asexually multiplied in Shasta County, Calif., and tested in the fruiting beds on the property of grower members of Driscoll Strawberry Associates, Inc. Clones of the seedlings were also held at the Propagation Nursery in Shasta County, Calif. One plant was selected from the aforementioned group of seedlings and further asexually reproduced in the Shasta County Nursery of Driscoll Strawberry Associates, Inc. Tests followed in various parts of California during interventing seasons on various properties of grower members of the Driscoll Strawberry Associates, Inc. These tests indicated the merits of the novel plant and resulted in its selection as a promising test variety.

FIG. 1 of the accompanying drawing illustrates plant parts of the new variety, typical in size, shape and color.

A berry in cross section illustrates flesh color and characteristic core activity. The inflorescence illustrates typical branching and relative size about the middle of July in Watsonville, Calif. The drawing shows the presence of three secondary peduncles with three ripe berries with the pedicel holding the primary berry originating from the axil of the secondary peduncles. There is also the presence of several leaflets originating from this axil, typical with this new variety. There is also illustrated a typical petiole, except that it does not show a bract present. The drawing does show two typical dark leaflets, a small bract leaflet and another funnel shaped bract leaflet originating with the other petiolules of the leaf. This funnel shaped bract is not found abundantly, but it can be found and is a distinguishing marker for the variety.

The novel plant of this everbearing variety is medium to large in size and vigor with the runner transplant as it comes from the nursery capable of producing a medium crown crop. It has the ability to continue producing the remainder of the year until the fall rains with a large total production. For an everbearer, this variety requires a minimum of cold storage before planting after being dug from the nursery, especially in comparison with Driscoll E18, Plant Pat. 3,529. The new variety is a vigorous runner producer, both at the nursery and the fruiting beds, especially if it is given more than the recommended chilling period in cold storage. If this new variety is planted during December or January, thhe main crop starts during the last of May, peaks during June and July, and gradually drops off in production until the fall rains prevent harvesting.

This novel cultivar plant distinguishes itself from other everbearing plants because it has a larger, more vigorously grown plant than most everbearers including the E18. The plant is larger, darker in color, produces more crowns per plant, its petioles are longer, it is a more prolific runner producer and its petiolules are longer than the E18. Its leaflets are not any larger and leaflet surface is less rugose. The plant often produces bracts on its petiole in

2 contrast to E18. The distinctive funnel shaped leaflet has never been observed on E18 and bracts on the petiole is rare on E18. The inflorescence of the new variety is slightly larger on the new variety, but both varieties have equal flower, fruit and calyx size during most of the year. The flower is visible above the plant during the late spring, but not strongly visible during subsequent crops, as is the case with E18. The pedicel holding thhe primary berry originates at the axil of secondary peduncles more often than does the E18. It is more common on the new variety to produce leaflets at the axil of secondary peduncles. The new variety generally produces a later crop in the fall than E18, but its fruit size may vary more when comparing plants of equal vigor and is lighter in color. The new variety is more prone to produce globular fruit than E18 and produces quaternary flowers that are sterile, but it normally produces enough pollen on other flowers to prevent malformed fruit. The epidermis firmness is considered good and has been equal to E18 in holding tests. The new variety is susceptible to two-spotted mite, but it is less susceptible to injury caused by this mite. The fruit dessert quality of the new variety is good, but not as good as E18. The limited tests on ascorbic acid content rates the new variety high, equal to that of E18. There is generally no aroma peculiar to the flesh of this variety. The new variety is moderately susceptible to mildew, equal in comparison to E18. It has the same level of susceptibility to the Mycosphaerella Leafspot as E18. It has not been completely tested against Verticillium and Red Seele diseases. As a seedling and selection, this variety withstood the natural invasions of certain virus components found in central California without losing its abiliy to produce.

The varietal characteristics of the novel plant, described below in detail, were observed mainly during the first fruiting season and the measurements and color descriptions were made during July in the Watsonville area of California which is a cool coastal area near the Pacific Ocean. The color terminology as used herein is in accordance with Ridgways Color Standards and Nomenclature (1912 Edition).

PLANTS

Medium to large for an everbearer, vigorous even under sandy soil conditions and has an extensive root system, producing multiple crowns by the end of the first fruiting season.

LEAVES

Medium in size. Central leaflet is usually 6 to 7 cm. in length with width slightly less. Petioles long and abundant. Petiolules are long, may be over 10 mm. in length. Serrations on leaflets are ovate in outline with a vivid acute apex. Leaflet color remains comparatively dark during fruiting season, but the early growth before cropping is distinctively lighter in color. The upper side of leaflet is Yew Green, Plate XXXI. Leaflet surface only slightly rugose and total leaflet cupped slightly upward. One leaflet may become like a funnel, especially on vigorously growing plants (see FIG. 1). Less than 1% of the plants may have leaves with this condition.

RUNNERS

Vigorous and prolific, both at the nursery and fruiting bed.

INFLORESCENCE

Medium to long in length, mostly 25 to 30 cm. during July. Common peduncle medium length 10 to 12 cm. during this period. Secondary peduncles are mostly two in number but 3 or 4 may be produced with two or three berries ripe on an inflorescence at one time. Considerable variation in fruit size between primaries and secondaries. Pedicel holding primary berry originates mainly at the axil of secondary peduncles, but may also branch from one of the peduncles near the axil. Anthers normally produce an abundance of pollen.

FRUIT

Crown crop berries are small to medium in size. Main crop is medium and large in size. Primaries mostly 37 to 42 mm. in length and 42 to 47 in width. Size becomes smaller during subsequent crops, especially secondary and tertiary berries. Shape of fruit is mainly medium wedge and medium conic to globose conic as described in USDA Bulletin 1043. Shoulders of fruit at the Calyx end are noticeably round, never necked. Surface mostly glossy, usually not ridged or rough with the seed held mostly at surface. Seeds mainly small to medium in size, are yellow, but turn dark if exposed to direct sunlight. The fruit surface color is Carmine, Plate I, and the flesh is Nopal Red, Plate I, to Scarlet, Plate I, at the core.

CALYX

Large in diameter, averaging 40 to 45 mm. The calyx is usually held irregularly near the fruit surface, but may become reflexed, especially shoulders of fruit are rounded with the calyx originating at a point below the perimeter of the fruit when observing the outline of the fruit from the size. Sepals of primary berries are usually serrated, overlay each other and are abundant. Sepals are mostly elliptical in outline, but may become ovate or obovate. The color of sepals on the side that faces the fruit is Dark, Dull Yellow-Green, Plate XXXII.

I claim:

1. The new and distinct variety of strawberry plant herein described and illustrated, and identified by the characteristics enumerated above.

No references cited.

ROBERT E. BAGWILL, Primary Examiner